United States Patent [19]

Tomoff et al.

[11] 4,413,534
[45] Nov. 8, 1983

[54] SAMPLE TRANSPORT MECHANISM

[75] Inventors: Toma Tomoff, Uberlingen; Hans G. Mohr, Uhldingen; Volker Kempf, Uberlingen, all of Fed. Rep. of Germany

[73] Assignee: Bodenseewerk Perkin-Elmer & Co., GmbH, Uberlingen, Fed. Rep. of Germany

[21] Appl. No.: 281,809

[22] Filed: Jul. 9, 1981

[30] Foreign Application Priority Data

Aug. 12, 1980 [DE] Fed. Rep. of Germany ....... 3030396

[51] Int. Cl.³ .................................................. G01F 35/06
[52] U.S. Cl. ........................... 73/864.21; 73/864.22; 73/864.25; 422/65
[58] Field of Search ........... 73/863.71, 863.72, 863.74, 73/864.22, 864.25; 422/65

[56] References Cited

U.S. PATENT DOCUMENTS

| 2,973,117 | 2/1961 | Conklin | 73/863.73 |
| 3,530,721 | 9/1970 | Hrdina | 73/864.22 |
| 3,748,911 | 7/1973 | Rousselet | 73/864.22 |
| 3,961,534 | 6/1976 | Gundelfinger | 73/864.84 |
| 4,111,051 | 9/1978 | Tamm et al. | |
| 4,140,018 | 2/1979 | Maldarelli | 73/864.22 |
| 4,294,126 | 10/1981 | Tomoff | 73/864.25 |
| 4,299,796 | 11/1981 | Esch | 422/65 |
| 4,312,591 | 1/1982 | Tomoff | |
| 4,363,798 | 12/1982 | Yamashita | 422/65 |

Primary Examiner—S. Clement Swisher
Attorney, Agent, or Firm—S. A. Giarratana; F. L. Masselle; R. A. Hays

[57] ABSTRACT

A mechanism for automatically supplying sample fluids to a chromatographic column is provided. The mechanism obviates the need for sealed sample containers as well as the need for pressurized gas commonly employed to force sample fluid from the sealed containers.

11 Claims, 8 Drawing Figures

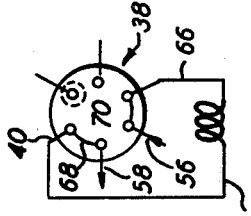
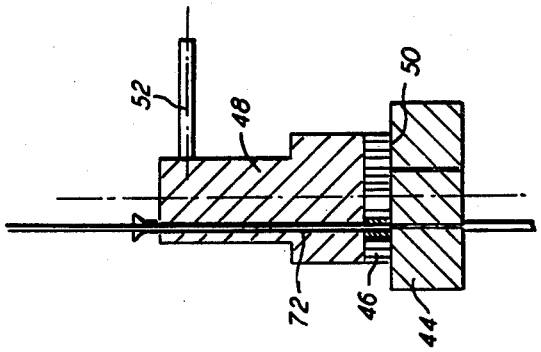
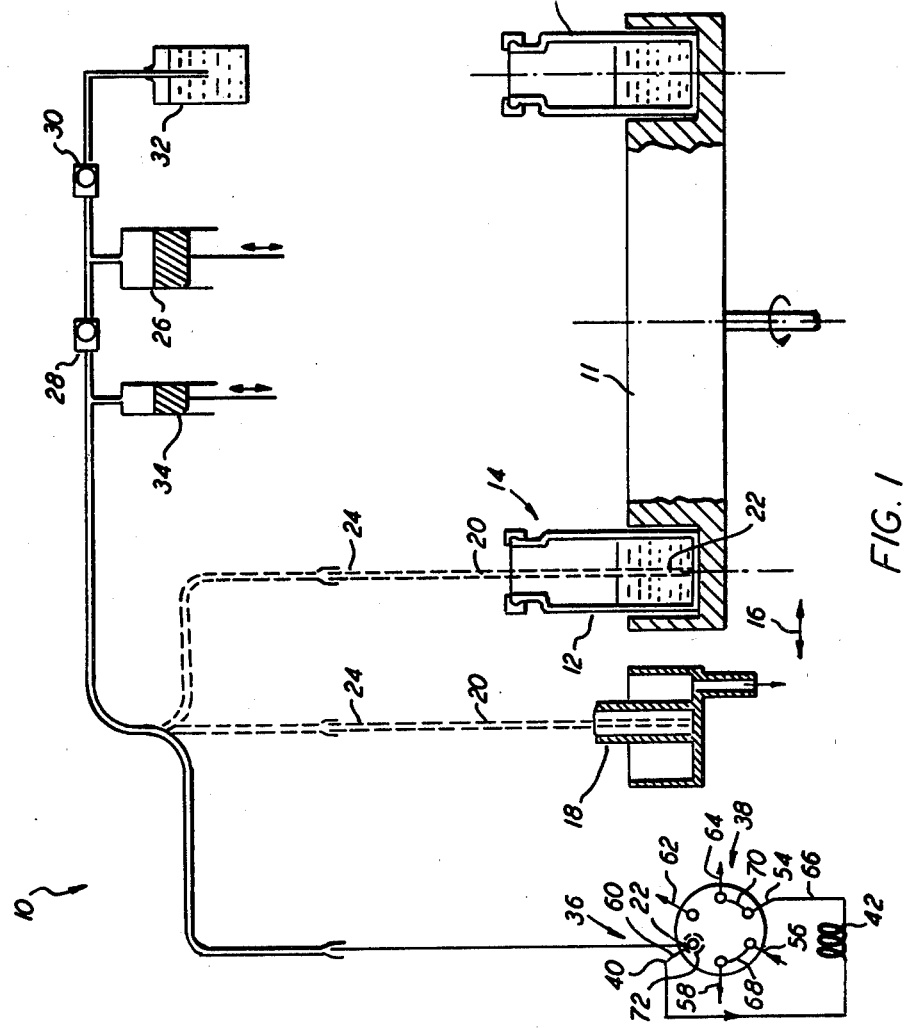

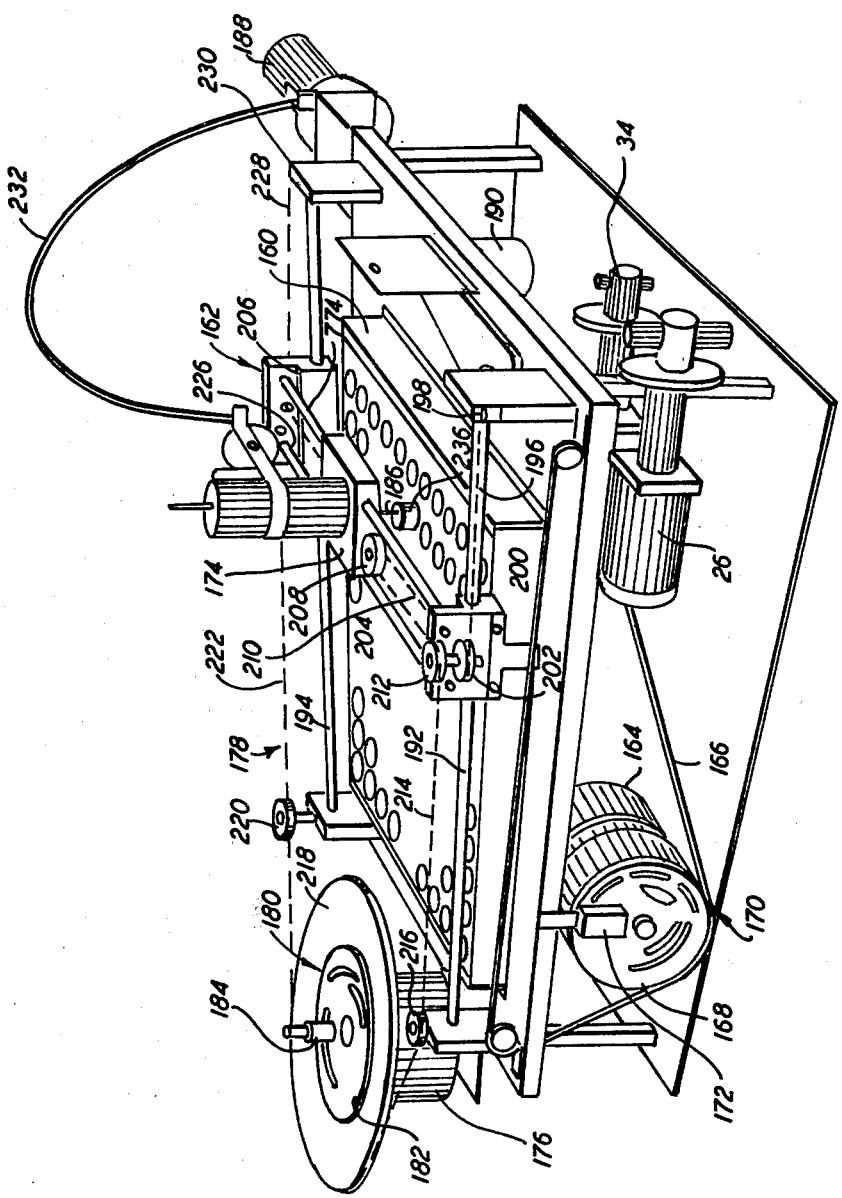
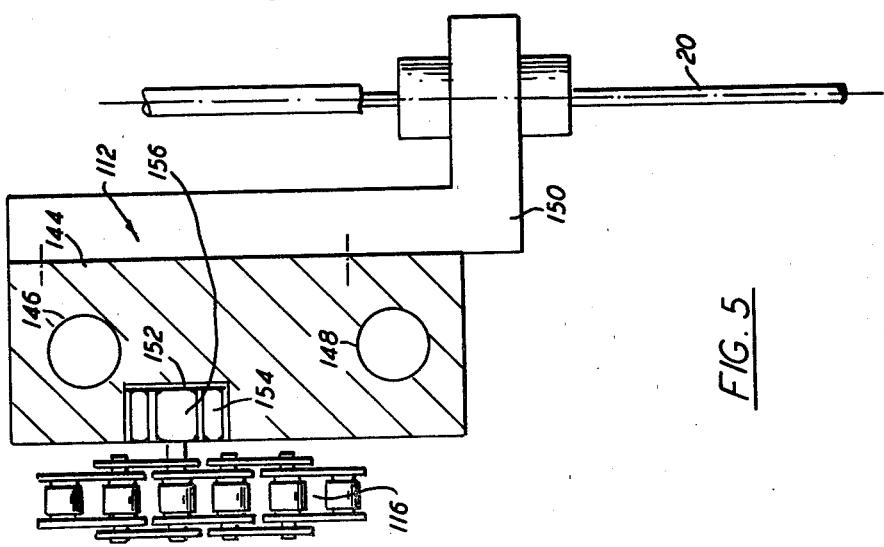
FIG. 7
FIG. 5

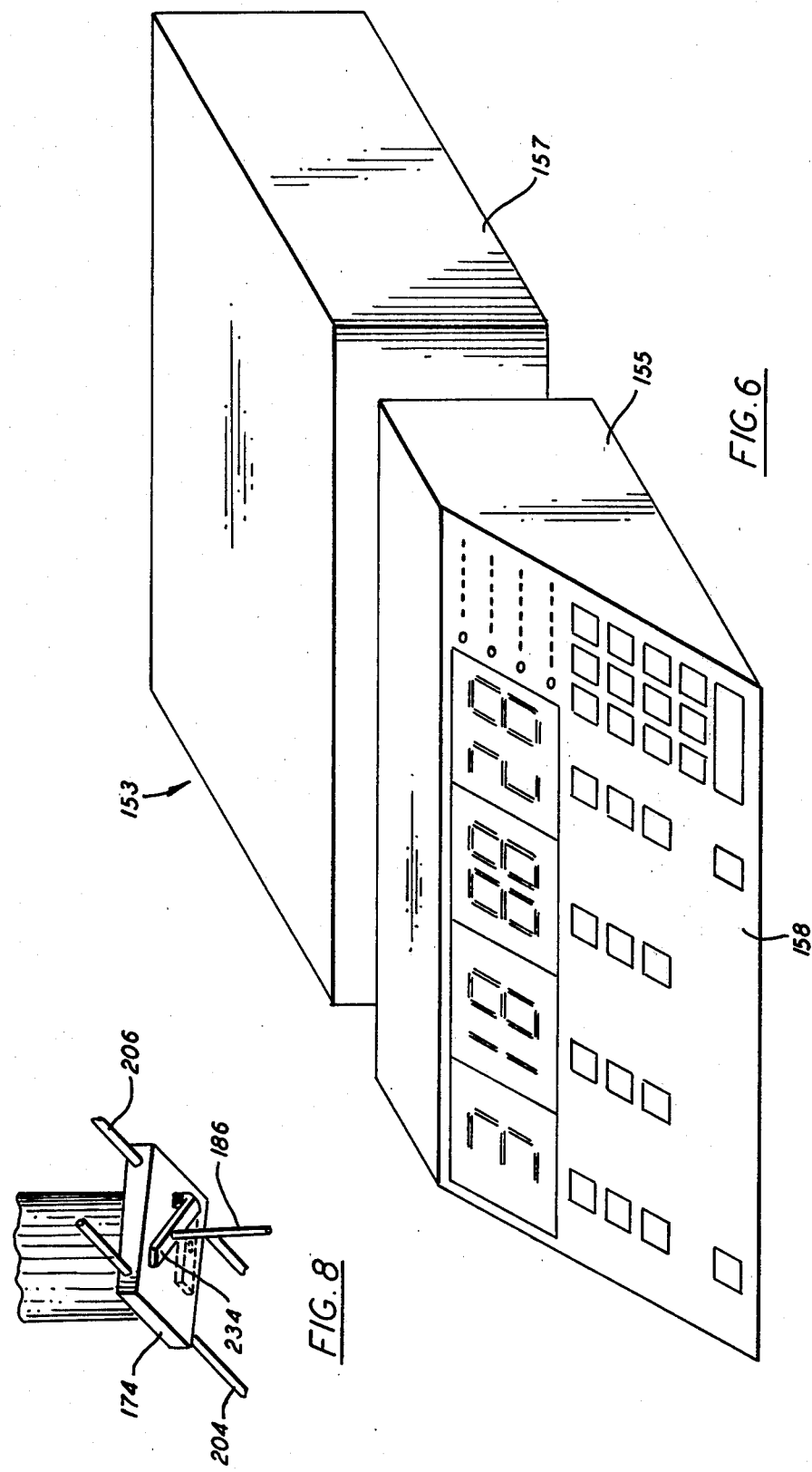

SAMPLE TRANSPORT MECHANISM

BACKGROUND OF THE INVENTION

The present invention generally relates to a mechanism for automatically supplying samples, and, in particular, relates to such a mechanism adapted for supplying a liquid sample to the measuring loop of a liquid chromatograph.

A liquid chromatograph comprises a separating column, through which a solvent is pumped. A liquid sample to be tested is inserted into this solvent flow and interacts with a separating substance present in the separating column. The sample substances are transported by the solvent flowing through the separating column with different transporting speeds depending on the strength of the interaction between the separating substance and the sample substance. Consequently, the components of the sample emerge successively from the exit of the separating column and can be captured individually, for example, by means of a fractional collector. The quantity of sample is supplied into the solvent fluid by means of a "measuring loop." The measuring loop is often a length of tube connected between a solvent pump and the entrance of the separating column, whereby the solvent flow through the tube carries the sample contained therein into the separating column.

In a prior art device for automatically supplying sample to the measured loop of a liquid chromatograph (Auto—Sampler Model 420 of The Perkin-Elmer Corporation, Norwalk, Connecticut) individual samples are contained in separate bottles, each of which is closed with a diaphragm, or septum. A needle, provided with two bores, pricks through the diaphragm and immerses with the lower bore into the sample. The upper bore of the needle remains above the liquid surface of the sample. Nitrogen is supplied under pressure into the bottle through the upper bore and the sample liquid is thus forced through the lower bore of the needle to a connecting conduit and the measuring loop. The measuring loop is then connected into the solvent flow of the chromatograph. The needle is removed from the bottle and is ready for the next sample.

The sample vessels described are required to be sealed by a diaphragm, which requirement involves considerable expenses. In addition, the transfer of the sample requires the availability of pressurized nitrogen. Another particular disadvantage in the prior art arrangement is that a considerable portion of the sample liquid is used for washing the needle, the connecting conduit and the measuring loop. Further, the dosing volume, i.e., the volume of the liquid sample actually supplied to the liquid chromatograph, is determined by the volume of the measuring loop and can be varied only by changing the measuring loop.

Devices for supplying samples to the graphite tube of a graphite tube atomizer in the flameless atomic absorption spectroscopy (see, for example, U.S. Pat. No. 4,111,051, issued on Sept. 5, 1978) or to a burner of a flameless atomic absorption spectrometer (see, for example, U.S. patent application Ser. No. 56,751, filed on July 12, 1979) are known, which devices are able to take in an accurately defined quantity of sample liquid from an open vessel and supply that quantity of liquid to the analytical instrument. To avoid cross-contamination between samples in these prior art instruments, the dosing tube thereof is washed inside and outside via a washing liquid prior to each sample feeding. For this purpose, the rear end of the dosing tube is connected via a washing liquid pump to a washing liquid container. After each sample feeding, the dosing tube is immersed into a washing vessel and washing liquid is pumped out of the washing liquid container through the dosing tube into the washing vessel. The sample liquid is sucked out of a sample vessel by means of a sample pump connected to the rear end of the dosing tube and supplied to the analytical instrument after a motion of the dosing tube.

SUMMARY OF THE INVENTION

Accordingly, it is one object of the present invention to provide a mechanism for automatically supplying sample fluid to the measuring loop of a liquid chromatograph, such that the sample is removed from an open vessel and whereby defined quantities of sample liquid can be supplied independently of the volume of the measuring loop and the sample liquid quantity required can be minimized.

The object is accomplished, at least in part, by an apparatus including a dosing pump which determines the quantity of liquid supplied to the measuring loop.

Other objects and advantages will become apparent from the following specification and the appended drawing.

BRIEF DESCRIPTION OF THE DRAWING

The present invention is hereinafter described with reference to the accompanying drawing wherein:

FIG. 1 is a diagramatic representation of an apparatus embodying the principles of the present invention.

FIG. 2 is a detailed view of a portion of the apparatus shown in FIG. 1.

FIG. 3 is a sectional view of the portion of the apparatus shown in FIG. 2.

FIG. 5 is a cross-sectional view of a portion of the mechanism in FIG. 4 and taken along the line 5—5 thereof.

FIG. 6 is a perspective illustration of a control unit for the apparatus.

FIG. 7 is a perspective illustration of another embodiment of the mechanism also embodying the principles of the present invention.

FIG. 8 shows a detail of the apparatus shown in FIG. 7.

DETAILED DESCRIPTION OF THE INVENTION

Figure 4:
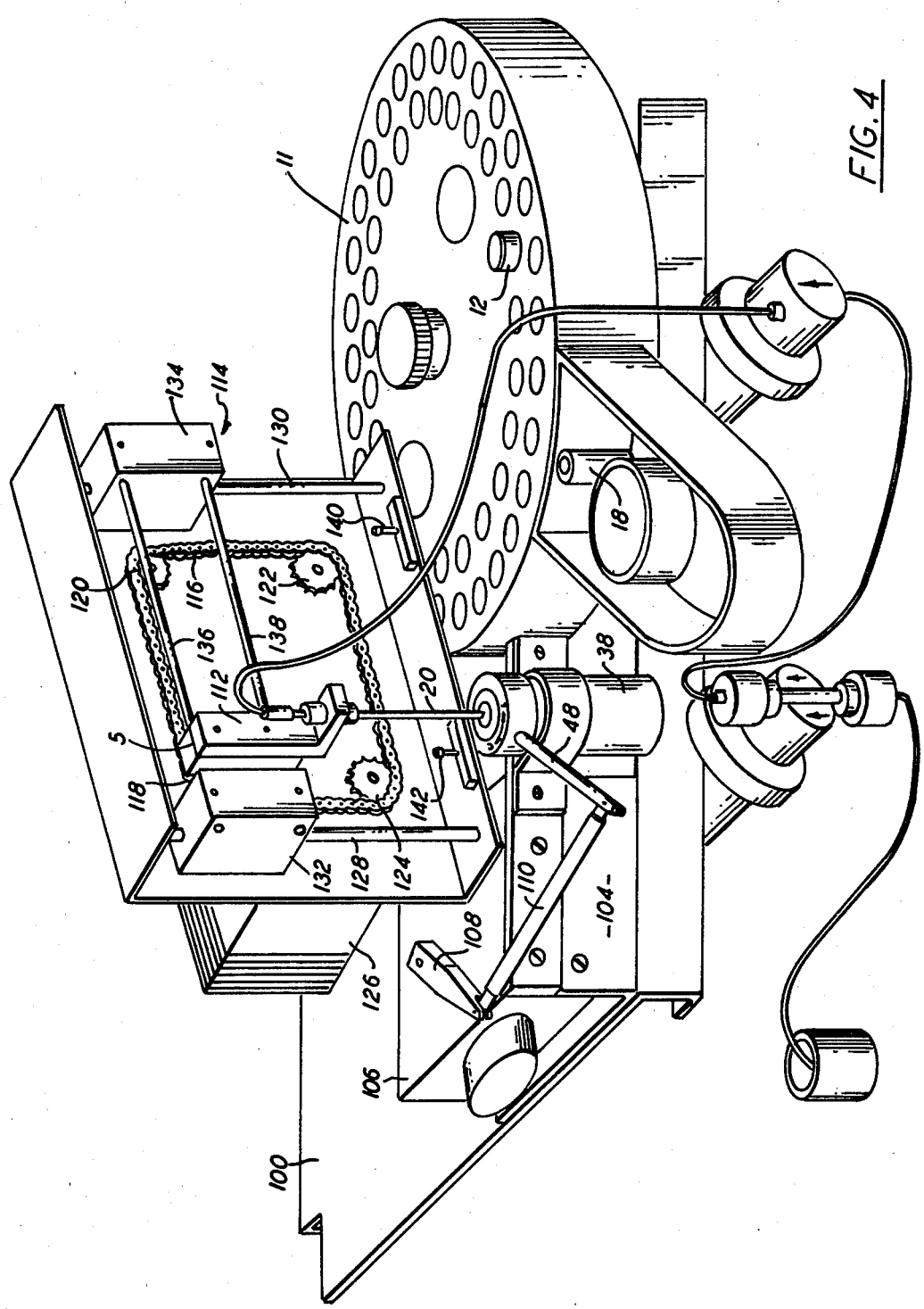
FIG. 4 is a perspective illustration of one embodiment of the invention.

An apparatus, generally designated by the numeral 10, embodying the principles of the present invention, includes a turnplate 11, which is representative of a transport mechanism for a plurality of sample vessels 12. The turnplate 11 successively transports the sample vessels 12 to a sample take-up station 14. The turnplate 11 is located on a support (not illustrated in FIG. 11), which is movable between first and second positions, indicated by the arrow 16. A washing vessel 18 is positioned on the support next to the turnplate 11. The washing vessel 18 is formed as an overflow vessel. In one position the sample vessel 12 is at the sample take-up station below a dosing tube 20. In another position the washing vessel 18 is so located below the dosing tube 20. The front end 22 of the dosing tube 20 can be selectively immersed into either the sample vessel 12 or the washing vessel 18, depending upon the position of the support.

The rear end 24 of the dosing tube 20 is connected via a washing liquid pump 26 and associated check valves 28 and 30 to a washing liquid vessel 32. In addition, the rear end 24 of the dosing tube 20 is also connected to a dosing pump 34, which selectively sucks in and discharges a predetermined quantity of liquid.

The dosing tube 20 is movable, in a manner more fully described below, between the sample take-up station 14, at which station its free front end 22 is immersed into a sample vessel 12 and a sample discharge station 36, at which station the free end 22 of the dosing tube 20 is connected, via a change-over valve 38, to one end 40 of a measuring loop 42.

Preferably, the change-over valve 38 is a rotary slide valve, including a stator 44 and a rotor 48 engaging the stator 44 with a sealing disc 46. The stator 44 and rotor 48 engage each other in a plane valving surface 50. The rotor 48 is rotatable between the first and second positions via, for example, a lever 52.

In FIG. 1, the change-over valve 38 is shown in its first position. In the preferred embodiment, the stator 44 has six ports 54, 56, 58, 60, 62 and 64 angularly spaced from each other by 60°. Preferably, two of the ports, 54 and 60, are diametrically opposite each other and are connected to two ends, 40 and 66 respectively, of the measuring loop 42. In addition, two ports, 62 and 64, are located between the two ports, 54 and 66, and are connected to outlets. One of the remaining ports, port 56, is connected to a solvent pump (not shown) and the sixth port, port 58, is connected to the chromatographic column (not shown). The rotor 48 further includes, in its control surface and packing disc 46, two connecting conduits, 68 and 70, each extending through 60° and angularly spaced from each other by 60°. At the sample discharge station 36 the free end 22 of the dosing tube is adapted to be connected to a port 72 of the rotor 48, which port opens into the valving surface 50 and which is angularly spaced from one of the connecting conduits by 60°.

In the position illustrated in FIG. 1, the entrance of the chromatographic column is connected via the connecting conduit 68 to the solvent pump. One end 40 of the measuring loop 42 is connected to the free end 22 of the dosing tube 20, whereas the other end 66 of the measuring loop 42 is connected through the connecting conduit 70 to the outlet. With a discharge stroke of the dosing pump 34 a quantity of liquid sample is sucked into the dosing tube 20 and pressed into the measuring loop 42 to displace the solvent present therein to the outlet. The measuring loop 42 can be filled up with sample liquid, to which end preferably a small excess of sample liquid is sucked in and delivered again by the dosing pump. It is, however, also possible to press a sample liquid quantity less then the volume of the measuring loop 42 thereinto.

In the second position of the changing-over valve 38, shown in FIG. 2, the free end 22 of the dosing tube 20 is connected through the port 72 of the rotor 48 and the port 62 of the stator 44 to an outlet. The solvent pump at port 56 of the stator 44 is connected through the connecting conduit 70 to the end 66 of the measuring loop 42. The other end 40 of the measuring loop is connected through the connecting conduit 68 of the rotor and the port 58 of the stator 44 to the chromatographic column.

Thus, the measuring loop 42 is connected between the solvent pump and the chromatographic column and the sample liquid quantity inserted into the measuring loop 42 is taken into the chromatographic column by the solvent flow.

The arrangement described above operates as follows:

The dosing tube motion, the dosing pump 34 and the washing liquid pump 26 as well as the turnplate 11 are synchronously controlled by a control unit. After a new sample vessel 12 has reached the sample take-up station 14, the dosing tube 20 is moved horizontally over the sample vessel 12 and then vertically thereinto. In this position, the free end 22 of the dosing tube 20 is immersed into the sample liquid and a quantity of sample liquid is sucked into the dosing tube 20 by the dosing pump 34. The dosing tube 20 is then moved upwards and laterally to the sample discharge station 36 and pushed into the rotor 48 of the changing-over valve 38, as illustrated schematically in FIG. 1 and constructionally in FIG. 3. The discharge stroke of the dosing tube 34 is now initiated whereby the sample liquid previously sucked in is pressed into the measuring loop 42. After changing over the changing-over valve 38 into its second position by means of a lever 52, the sample liquid supplied to the measuring loop 42 is pressed into the chromatographic column by the solvent flow.

The dosing tube 20 can then be pulled upwards out of the rotor 48 of the changing-over valve 38. The support (not shown in FIG. 1) is moved into its second end position, such that the sample vessel 12 is no longer at the sample take-up station 14 below the dosing tube 20 but the washing vessel 18 is so located. The dosing tube 20 is immersed into the washing vessel 18. Washing liquid is pumped out of the washing liquid container 32 through the dosing tube 20 into the washing vessel 18 by the washing liquid pump 26. A sufficient quantity of washing liquid is delivered whereby the washing vessel 18 overflows. Thus, the free end of the dosing tube 20 is thoroughly cleaned, on both the outside and inside, of any residue of the previously delivered sample. The dosing tube 20 is then pulled out of washing vessel 18. The dosing pump 34 now sucks a small quantity of air into the dosing tube 20, which air serves as a pocket to separate the sample liquid subsequently sucked in from the washing liquid.

Simultaneously, the turning plate 11 is rotated, preferably by one step. Thus, when the support is returned to its first position, the next sample vessel 12 is at the sample take-up station 14. The dosing tube 20 is moved down again and immerses, as described, with its free end 22 into the sample liquid. The next sample is now sucked into the dosing tube 20 in the manner already described.

One particularly advantageous, constructive embodiment of the above-described apparatus 10 is perspectively illustrated in FIG. 4.

On a base plate 100 the turnplate 11 is rotatably and pivotably mounted. The turnplate 11 comprises, for example, forty bores, into which a plurality of sample vessels 12 can be inserted. The washing vessel 18 is pivotable with the turntable 11. The turntable 11 with the projection comprising the washing vessel 18 forms the "support" mentioned above. The changing-over valve 38 is mounted on the base plate 100 by means of a bracket 104. A pneumatic servomotor 106 with a pivoting lever 108, is located in the same bracket 104;

the pivoting lever 108 being connected to the lever 48 of the valve 38 via a linkage 110.

The dosing tube 20 is vertically attached to a dosing tube holder 112. Means 114 are provided for holding the dosing tube holder 112 vertical while permitting both vertical and horizontal movement thereof. A driving chain 116 is tightly guided around four sprocket wheels 118, 120, 122 and 124 arranged in the corners of a rectangle having vertical and horizontal sides, one wheel of which is adjusted to be driven by a servomotor 126. The dosing tube holder 112 is connected to the driving chain 116 as illustrated in FIG. 5.

The holding means 114 includes a pair of vertical sliding bars 128 and 130 laterally spaced from each other and a pair of blocks, 132 and 134, which blocks, 132 and 134, are guided on one of the vertical sliding bars, 128 and 130. A pair of horizontal sliding bars 136 and 138 are arranged between the blocks 132 and 134 and are vertically spaced from each other in plane parallel to the plane of the vertical sliding bars 128 and 130. The dosing tube holder 112 is guided on these horizontal sliding bars 136 and 138 by means of any appropriate guiding means. The dosing tube holder 112 can thus move horizontally on the sliding bars 136 and 138 and vertically on the blocks 132 and 134 with the bars 136 and 138 and the dosing tube holder 112 on the vertical sliding bars 128 and 130. When the driving chain 116 is caused to move, the dosing tube holder 112 thus moves horizontally or vertically along with the driving chain 116. In FIG. 4, the sample take-up station is on the right and the sample discharge station is on the left. The dosing tube holder 112 with the dosing tube 20 moves horizontally between these two stations, the holder 112 moving vertically downwards upon reaching the respective station. The downward motion of the dosing tube holder 112 is limited by adjustable stops 140 and 142, respectively, at the sample take-up station 14 and the discharge station 36.

As can be seen from FIG. 5, the dosing tube holder 112 comprises a block 144 having two parallel bores 146 and 148 therein by which the dosing tube holder 112 is guided on the sliding bars 136 and 138. A bracket 150 is provided on the block 144, to which bracket 150 the dosing tube 20 is retained at its rear end 24. The block 144 includes a recess 152 having a roller bearing 154 therein, which bearing 154 is engaged via an elongated bolt 156 to the driving chain 116.

The operating sequence is determined by a control unit 153. The control unit 153 consists of two assemblies 155 and 157 adapted to be specially separable, one of which, for example 155, comprises the operation and display field 158 only and the other, 157, comprises a microprocessor and the associated interfaces. This separation ability offers the practical advantage that the assembly 155 with the operation and display field 158 can be arranged at a distance from the liquid chromatograph and from the described arrangement for supplying sample.

FIGS. 7 and 8 depict a modified embodiment of the mechanical construction. In the embodiment of FIGS. 7 and 8, the sample vessels are arranged in a stationary holder 160 of generally rectangular shape in rows parallel to each other such that each sample vessel can be characterized by a row and a column number. In this embodiment, the holder 160 is stationary and the dosing tube 186 is moved relative thereto. To this end a cradle 162, extending parallel to the rows is movable guided above the holder 160 in a direction perpendicular to the rows. The cradle 162 is adjustable by a first servomotor 164 through a rope transmission 166. The position of the servomotor 164 is controlled by a first coding device 168, which, in one instance, consists of a coded disc 170 located on the shaft of the servomotor 164 and of a light barrier arrangement 172. A carriage 174 is movably guided on the cradle 162 along the rows, which carriage 174 is adjustable by a second servomotor 176 through a rope transmission 178. The position of the servomotor 176 can be controlled by a second coding device 180. The second coding device 180 consists of a code disc 182 and a light barrier arrangement 184. The dosing tube 186 is vertically movable by a third servomotor 188. The cradle 162 and the carriage 174 are movable to a position beside the holder 160, in which position the dosing tube 186 is located above the sample discharge station, where a valve 190 of the type of FIG. 3 is arranged.

The second servomotor 176 is stationary with respect to the apparatus on one side of the holder 160. The cradle 162 is guided on two parallel guiding bars 192 and 194. The rope transmission 178 assigned to the second servomotor 176 comprises a rope 196, which is held stationary with respect to the apparatus at one end 198 on the side remote from the servomotor 176. The rope 196 extends with one rope section 200 along one sliding bar 192 and is deviated about a first deviating roller 202 provided on one side at the cradle 162. The rope 196 is then guided along the guide means of the carriage 174, which guide means is preferably formed by two sliding bars 204 and 206, to a second deviating roller 208 provided thereon. The rope 196 is deviated by 180° by the second deviating roller 208 and is guided in the one rope section 214 along a sliding bar 192. The rope 196 is then deflected around a roller 206 and wound around a pulley 218 mounted on the servomotor 176. The rope 196 also extends around a deviating roller 220 and in a rope section 222 along the other sliding bar 194. The rope 196 then passes (in a manner not illustrated) similar as on the front side in FIG. 7, about a fourth deviating roller provided on the other side on the cradle 162, is deviated thereby and guided along the guide means, 204 and 206, of the carriage 174 in a rope section 224 to a fifth deviating roller (not visible) provided on the carriage 174. The rope 196 is again deviated through 180° by the fifth deviating roller and guided, in a rope section 226, to a sixth deviating roller provided on the cradle 162 and coaxial to the deviating roller. The rope is deviated thereby and guided, in a rope section 228 along the other sliding bar 194 and held stationary with respect to the apparatus, with the other end 230 on the side remote from the servomotor 176.

With such a rope transmission it is possible that the servomotor 176 can be arranged stationary with respect to the apparatus. The cradle 162 can thus be moved along the sliding bars 192 and 194 by the servomotor 164 without affecting the position of the carriage 174 relative to the cradle 162. The carriage 174 is moved, again without affecting the position of the cradle 162, by the servomotor 176. Defined, discrete positions of the cradle 162 and the carriage 174 are predetermined by the coding devices 170 and 180, which positions correspond to a vessel in the holder 160. Thus, the dosing tube 186, together with the carriage 174, can be moved over each sample vessel in the holder 160.

The third servomotor 188 is also arranged stationary with respect to the apparatus. The downward and upward motion is transmittable from the third servomotor 188 to the dosing tube 186 via, for example, a Bowden wire 232.

As illustrated in FIG. 8, a device 234 for holding down a vessel is provided on the carriage 174, which device 234 holds down the sample vessel 236, while the dosing tube 136 is retracted in the event closed sample vessels 236 (FIG. 7) covered by a septum are used. In order to prevent the device 234 from interfering with the insertion of the dosing tube 186 into the changing-over valve 190 at the sample discharge station, the device 234 is pivotably mounted. Thus, at the sample discharge station the device 234 is automatically deflected into the position illustrated in dotted lines.

While the present invention has been described herein with respect to a particular embodiment, other arrangements which are within the spirit and scope of this invention will become apparent from a reading hereof. Thus, the invention herein is considered to be limited solely by the claims appended hereto and the reasonable interpretation thereof.

What is claimed is:

1. Mechanism for automatically supplying sample from sample vessels to a measuring loop of a liquid chromatograph; said mechanism comprising:
    a stationary holder arranged to retain said sample vessels in rows parallel, whereby each sample vessel can be characterized by a row and a column number;
    a dosing tube, said tube having a front end and a rear end; said dosing tube being vertically movable by a third servomotor;
    a changing-over valve having a plurality of ports;
    a measuring loop, said measuring loop being connected to a first port and a second port of said changing-over valve;
    a solvent pump outlet, said solvent pump outlet connecting to a third port of said changing-over valve,
    means for positioning said dosing tube between a first position whereat said front end thereof is in one of said sample vessels and said rear end thereof communicates with a dosing pump whereby sample fluid can be sucked into said dosing tube, and a second position whereat said front end thereof communicates with said first port of said changing-over valve and whereat said dosing pump discharges said sample from said dosing tube into said measuring loop;
    a control unit for controlling and synchronizing said changing-over valve with said dosing tube position whereby when said dosing tube is in said first position thereof said solvent pump communicates with said column and when said dosing tube is in said second position thereof said solvent pump communicates with said column via said measuring loop;
    a cradle extending parallel to said rows is movably guided above said holder in a direction perpendicular to said rows by a first servomotor via a rope transmission, wherein the position of said first servomotor being controlled by a first coding device;
    a carriage movably guided on said cradle along said rows, said carriage being adjustable by a second servomotor via a rope transmission, said second servomotor being controlled by a second coding device,
    said cradle and said carriage being movable into a position beside said holder, whereat said dosing tube is located above the sample discharge station;
    said second servomotor being stationary with respect to the apparatus on one side of the holder,
    said cradle being guided on two parallel sliding bars; and
    said rope transmission assigned to the second servomotor comprises a rope, which:
    is retained stationary with respect to the apparatus with one end on the side remote from the servomotor and extends along one sliding bar;
    is deviated around a first deviating roller provided on one side of said cradle and being guided along the guide means of said carriage to a second deviating roller provided thereon;
    is deviated through 180° by said second deviating roller and guided to a third deviating roller provided on said cradle and being coaxial to said first deviating roller;
    is deviated thereby and guided further along one sliding bar;
    winds around a pulley located on said second servomotor;
    then extends along the other sliding bar;
    is deviated around a fourth deviating roller provided on the other side of said cradle and guided along said guide means of said carriage to a fifth deviating roller provided thereon;
    is deviated through 180° by said fifth deviating roller end guided to a sixth deviating roller provided on said cradle and coaxial to said fifth deviating roller,
    is deviated thereby and guided further along the other sliding bar and also being stationary with respect to the apparatus with the other end on the side remote from the servomotor.

2. Mechanism as claimed in claim 1 further comprising:
    a washing liquid pump, said washing pump connecting, via an intake port to a washing liquid vessel and, via a discharge port, to said rear end of said dosing tube, said dosing tube simultaneously being positioned over a washing vessel; and
    a washing process being initiated after each sample intake by said control unit during which process said tube is moved to an operational position: said washing pump providing washing liquid from said washing liquid vessel through said dosing tube into said washing vessel.

3. Mechanism as claimed in claim 2 wherein:
    said sample vessels are successively movable to a sample takeup station by a transport mechanism, said transport mechanism and said washing vessel being arranged on a carrier movable between two positions whereat in said one position of said carrier a sample vessel is located at said sample take-up station below said dosing tube;
    in said second position of said carrier said washing vessel is moved to this position; and
    said carrier being movable to said second position washing vessel is moved to this position; and
    said carrier being movable to said second position and said dosing tube being movable to said sample takeup station by said control unit for establishing the operational position "washing."

4. Mechanism as claimed in claim 1 wherein:
    said changing-over valve is a rotary slide valve including a stator and an engaging rotor with a plane valving surface;
    said stator having six ports angularly spaced from each other by 60°, of which:

two ports diametrically opposite each other are connected to the two ends of said measuring loop;

two ports located on one side between said ports are connected to outlets;

one of the other ports is connected to a solvent pump; and the sixth port is connected to said chromatographic column;

said rotor in said valving surface includes two connecting conduits extending through 60° each and angularly spaced from each other by 60°; and said free end of said dosing tube at said sample discharge station is arranged to be connected to a port of said rotor which port opens into said valving surface and which is angularly spaced from one of said connecting conduits by 60°.

5. Mechanism as claimed in claim 4, wherein said rotor is movable between two positions angularly spaced from each other by 60° by a servomotor, such that:

in one position the port arranged to be connected to said dosing tube is aligned with a port of said stator, connecting to one end of said measuring loop; and in the other position said port of said stator communicates through one of said connecting conduits with the port of said stator connecting with said chromatographic column.

6. Mechanism as claimed in claims 1 or 5, wherein:

said dosing tube is vertically attached at a dosing tube holder;

means for holding said dosing tube holder parallel while permitting vertical and horizontal movement;

a driving chain is tightly guided around four sprocket wheels arranged in the corners of a rectangle with vertical and horizontal sides, one wheel of which is arranged to be driven by a servomotor; and said dosing tube holder is connected to said driving chain.

7. Mechanism as claimed in claim 6, wherein said holding means includes a pair of vertical sliding bars laterally spaced from each other;

a pair of blocks guided on one of said vertical sliding bars each;

a pair of horizontal sliding bars arranged between said blocks vertically spaced from each other in a plane parallel to the plane of the vertical sliding bars; and means for sliding said dosing tube holder is guided on the horizontal sliding bars.

8. Mechanism as claimed in claim 1 wherein the downward motion of said dosing tube holder is limited by adjustable stops.

9. Mechanism as claimed in claim 8 wherein:

said control unit includes two separate assemblies, one of which comprises only the operation and display field and the other one comprises a microprocessor and the associated interfaces.

10. Mechanism as claimed in claim 1 wherein:

said third servomotor is arranged stationary with respect to the apparatus; and the upward and downward motion is transmitted from the third servomotor to the dosing tube through a Bowden wire.

11. Mechanism as claimed in claim 10 wherein:

a device for holding down a vessel is provided on said carriage, which device holds said sample vessel while said dosing tube is pulled back, and said device for holding down a vessel is pivotably mounted and automatically deflected at said sample discharge station.

* * * * *